US00PP11012P

United States Patent [19]

Reisch et al.

[11] Patent Number: Plant 11,012

[45] Date of Patent: Jul. 20, 1999

[54] GRAPE CULTIVAR 'MARQUIS'

[75] Inventors: Bruce I. Reisch; Robert Pool, both of Geneva; George Remaily, Hammondsport; John Einset, deceased, late of Geneva, all of N.Y., by Hjordis Einset, executrix

[73] Assignee: Cornell Research Foundation, Inc., Ithaca, N.Y.

[21] Appl. No.: 08/934,652

[22] Filed: Sep. 23, 1997

Related U.S. Application Data

[63] Continuation of application No. 08/653,948, May 21, 1996, abandoned.

[51] Int. Cl.[6] ..... A01H 5/00

[52] U.S. Cl. ..... Plt./207

[58] Field of Search ..... Plt./47.3, 205, Plt./206, 207

*Primary Examiner*—Howard J. Locker

[57] ABSTRACT

A new and distinct variety of grapevine (Vitis interspecific hybrid (*V. vinifera, V. labrusca*)) named 'Marquis' and tested as NY64.029.01, which originiated as a cross of 'Athens' and 'Emerald Seedless' is described. This new variety can be distinguished by its large normally yellow-green berries borne on large clusters, excellent flavor, and good cold hardiness. It offers growers and consumers a large, attractive, flavorful fruit that serves as a seedless table grape.

3 Drawing Sheets

CROSS-REFERENCE TO RELATED APPLICATIONS

This application is a continuation of Application Ser. No. 08/653,948, filed May 21, 1996, now abandoned.

BACKGROUND OF THE INVENTION

Grape cultivar NY64.029.01 was developed by a breeding program in the Department of Horticultural Sciences, Cornell University, New York State Agricultural Experiment Station, Geneva, N.Y. as a seedless table grape. This new cultivar resulted from the hand pollinated cross of 'Athens' (non-patented) with 'Emerald Seedless' (non-patented). The cross was made in 1964, and 17 seedling vines were grown from seed in 1968 and planted to a permanent vineyard site (Vineyard 40, Row 63, Lucey Farm, Sutton Road, Geneva, N.Y.) on May 5, 1969. Fruit were first observed in 1974 and the original vine was vegetatively propagated for further testing in 1980. The original vine was propagated by rooting of dormant hardwood cuttings (February 1980) in a greenhouse in Geneva, N.Y. and the rootings were transplanted as rooted plants to a field nursery locations (Geneva, N.Y.) in the late Spring, 1980. The nursery grown vines were transplanted in the Spring, 1981, to a permanent vineyard site on the Crittenden Farm, Geneva, N.Y., for further testing.

NY64.029.01 has been named and will be released as 'Marquis' and is the subject of this invention.

DESCRIPTION OF RELATED ART

The vines of 'Marquis' are moderately winter hardy at Geneva and trunk injury has not been observed through the end of 1995. Bud cold hardiness ranks at least with 'Himrod' and other relatively cold hardy seedless grapes. In April, 1990, 'Marquis' had 4% shootless nodes, while 'Himrod', 'Canadice', 'Einset Seedless' and 'Chardonnay' had 18%, 11%, 19% and 60% shootless nodes, respectively. In May, 1989, 'Marquis' had 18% shootless nodes, while 'Himrod', 'Canadice', 'Einset Seedless' and 'Lakemont' had 17%, 29%, 17%, and 81% shootless nodes, respectively.

Bud break in the Spring occurs with or slightly after Concord.

BRIEF DESCRIPTION OF THE DRAWINGS

The accompanying photographs show typical specimens of the fruit and leaves of the new variety in color as nearly true as it is reasonably possible to make in a color illustration of this character.

DESCRIPTION OF THE INVENTION

Figure 1:
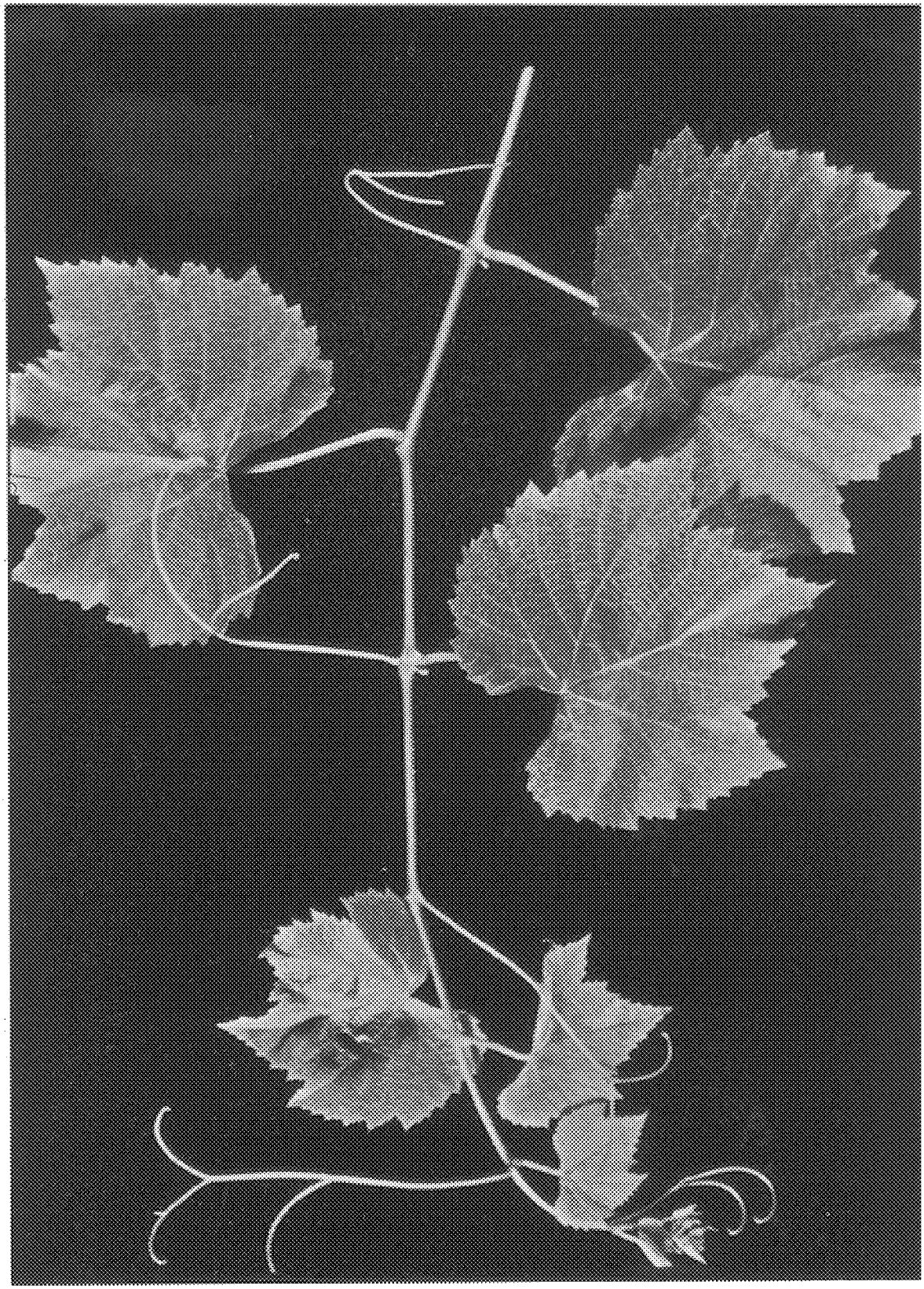
FIG. 1. Growing shoot of 'Marquis'.

This invention relates to a new and distinct cultivar of grape, 'Marquis' which was discovered in a test planting belonging to the New York State Agricultural Experiment Station, Cornell University, Geneva, Ontario County, N.Y. This discovery is a product of a grape breeding research program of the New York State Agricultural Experiment Station.

'Marquis' is distinguished by its large berries borne on large clusters, excellent flavor and good cold hardiness.

Own-rooted vines of 'Marquis' grown in phylloxera (*Daktulosphaira vitifoliae* Fintch.) infested soils are productive and moderately vigorous. Pruning weights averaged between 1.1 and 1.4 kg cane prunings from 1990 to 1995 in southwestern Michigan (grown as "restricted test variety" by Southwest Michigan Research and Extension Center, Michigan State University, Benton Harbor, Mich. 49022). During this period fruit yields ranged from approximately 9 to 20 metric tonnes/hectare (4 to 9 tons/acre). In 1995, vines which were thinned to one flower cluster per shoot produced a mean yield of 11 metric tonnes/hectare (5 tons/acre). Since vines have been adequately vigorous on their own roots, they have not been tested on commercial rootstocks. However, due to its *Vitis vinifera-Vitis labrusca* (non-phylloxera resistant) ancestry, vines should be grafted to a phylloxera resistant rootstock in areas with severe phylloxera pressure.

Flowers of 'Marquis' are perfect, self-fertile, and bloom in mid-season. For 'Marquis' grown at Geneva, N.Y., date of 50% bloom was Jun. 22, 1996, Jun. 28, 1997, and Jun. 14, 1998 or one, four and seven days later than date of 50% bloom for 'Concord' in 1996, 1997 and 1998, respectively.

Clusters are shouldered, large and moderately loose with large (3.0 to 5.0 gm), normally yellow-green, spherical berries. Berries weighed 5.4 grams each in Arkansas in an irrigated research vineyard ( grown as a restricted test variety by the University of Arkansas). Weight per cluster ranges from 0.27 to 0.61 kg. Very little crop is borne on lateral shoots and cluster thinning is required due to the large cluster size. 'Marquis' ripens between 15 and 30 Sept. in Geneva, N.Y.; in this region, there are usually 80 to 90 days between bloom and harvest. The flavor is very mild Labrusca, but it develops a richer American flavor if left to ripen another 5–10 days. The skin is thick, flesh is melting and very juicy and the seed traces are medium in size and soft. The skin softens as the berries continue to ripen. Clusters are highly sensitive to gibberellic acid applications which causes berry drop and distorted, thickened rachises. Cane girdling and flower cluster thinning can be used effectively to increase cluster compactness and number of berries per cluster. In addition, flower cluster thinning results in an increase in berry weight. Juice soluble solids range between 14 and 19 °Brix when ripe, and the acidity is very low, 3.6 gm/liter (at 18.6 °Brix) in southwestern Michigan in 1995.

Foliage and fruit are susceptible to powdery mildew (*Uncinula necator* [Schw.] Burr.), downy mildew (*Plasmopara viticola* [Berk. and Curt.] Berk. & de Toni) and black rot (*Guignardia bidwellii* [Ellis] Viala Ravaz), but moderately resistant to Botrytis bunch rot (*Botrytis cinerea* [Pres.]). Heavy rainfall during the ripening period may result in skin cracking at the distal end of the berry.

The following is a detailed description of the viticultural characteristics of 'Marquis'. Color terminology is in accordance with that of The "Royal Horticultural Society Colour Chart" published in 1966 by The Royal Horticultural Society of London, England. When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

The descriptions reported herein, unless otherwise stated, are from specimens vegetatively propagated and grown at Geneva, N.Y.

Vine: Vigorous, with weight of cane prunings/vine/year between 0.5 and 1.0 kg, upright to slightly trailing in growth habit. Bud break takes place at the same time as 'Concord' or slightly later. The trunk is moderately strong. The trunk of 'Marquis' sheds bark in medium-narrow longitudinal strips. Bark color ranges (approximately) from greyed-orange 177B to brown 200D on lighter bark sections to black 202A/202B on darker sections. On head-trained, cane-pruned vines, the internode length on bearing canes was found to average 7.6 cm. Optimum training system has not been determined.

Shoot tip: Slightly curved with white felty indument (FIG. 1). The first flat leaf is also covered with white felty indument (157D).

Shoot: Very little lateral shoot production occurs. Trendrils are slender, branched, wiry, and discontinuous along the shoot.

Figure 2:
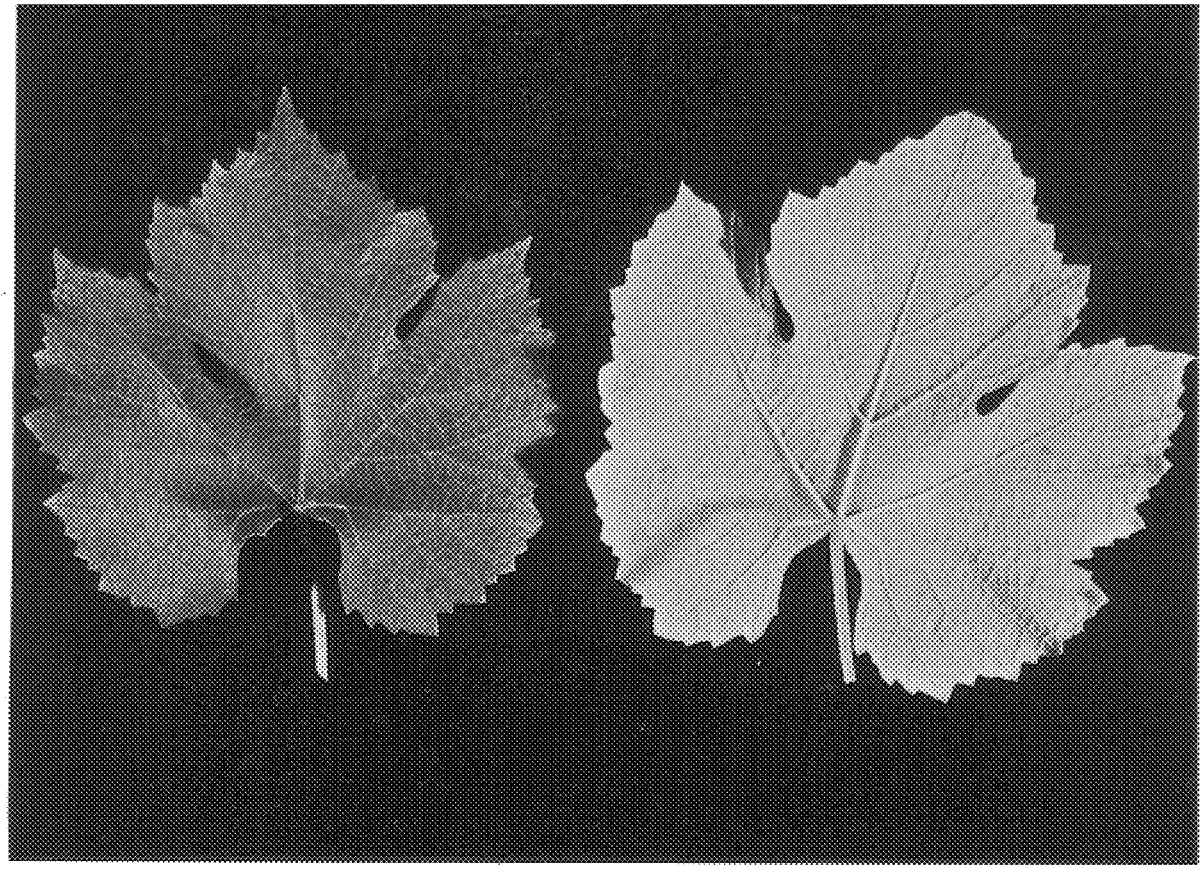
FIG. 2. Mature Leaf: upper leaf surface at left, and lower leaf surface at right.

Mature leaves: Leaves are cuneo-truncate with moderate sized lyre-shaped petiolar sinuses (FIG. 2). Superior sinuses range from very shallow, v-shaped to narrow and club-shaped. Upper leaf surface is glabrous, flat, smooth, and green 137B. The lower leaf surface is felty, flat smooth and green-white 157D. Dentation consists of convex teeth of average width. Leaves of 'Marquis' are moderately sized or medium following the standard terminology in Galet, "A Practial Ampelography" (1979).

Figure 3:
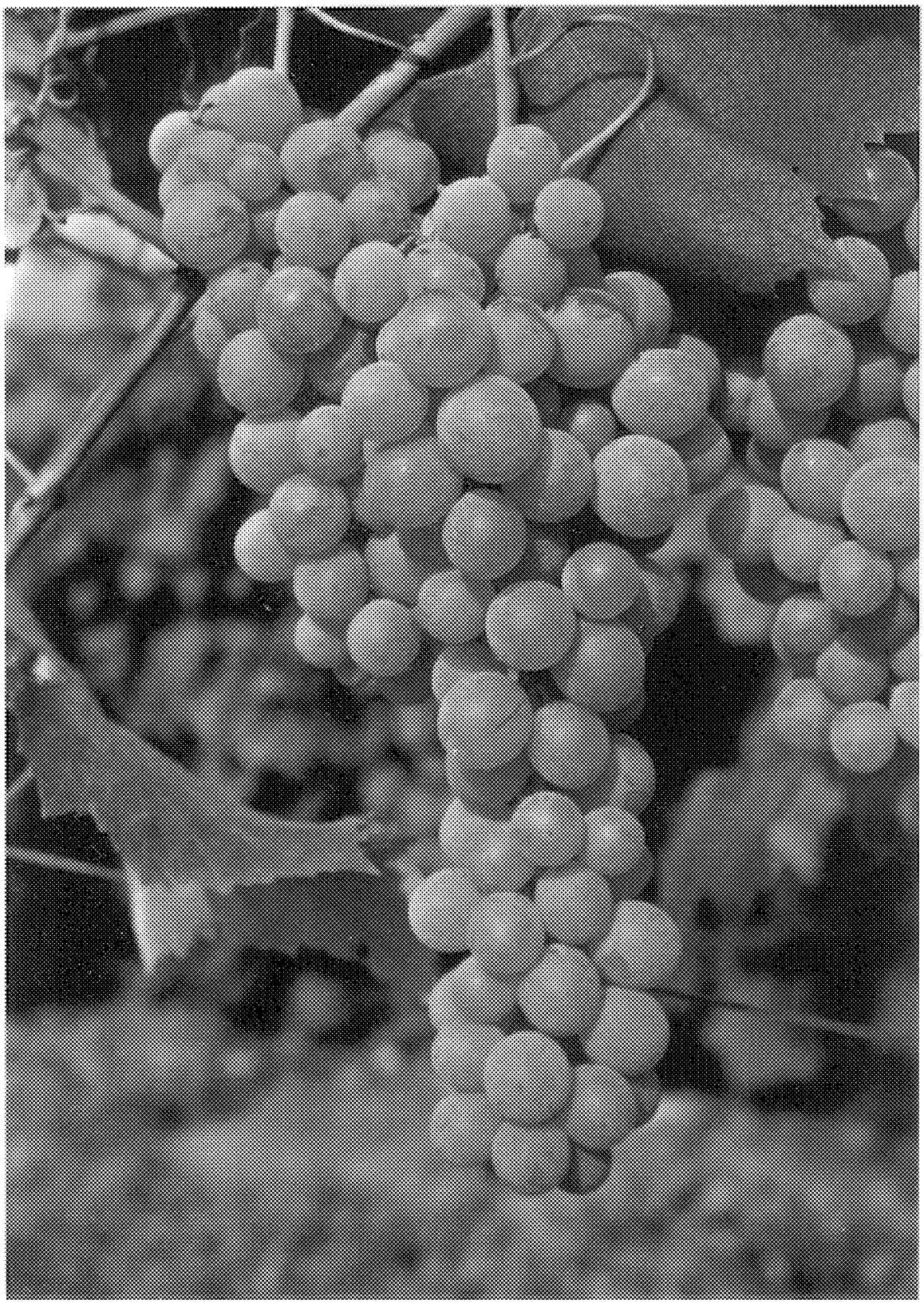
FIG. 3. Fruit cluster of 'Marquis'.

Clusters: Shouldered, medium large, 270 to 610 grams/cluster, usually borne 2 per shoot on primary shoots (FIG. 3). Very little crop is borne on lateral, secondary, and tertiary shoots. Clusters are moderately loose.

Stems: The stem diameter on one-year-old canes was found to be 5.9 mm and the stem color was approximately greyed-orange 177A to 177B.

Fruit: Large (3.0 to 5.0 grams/berry) and spherical in shape, with medium sized soft seed remnants, maturing between 15 and 30 September in Geneva. The skin is medium tough, slightly susceptible to cracking when wet and yellow-green 145B (to yellow 11C in sun exposed fruit) with a light waxy bloom. As the fruit continue to ripen on the plant, they may take on tones of amber. No color changes hae been noted in post-harvest after ripening. In Benton Harbor, Mich., pre-bloom cluster thinning to one cluster per shoot resulted in increases in fruit cluster weight and berry weight; cluster weight increased from 262 to 367 grams per cluster, berry number from 60 to 81 berries per cluster, and berry weight from 4.3 to 4.8 grams per berry. Berry flesh texture is soft and melting to juicy compared to berry flesh of *Vitis vinifera* (often firm) and to berry flesh of *Vitis labrusca* (tough, chewy, slippery). The skin of 'Marquis' berries is thinner than skin of *Vitis labrusca* berries but thicker than skin of typical *Vitis vinifera* table grapes. The skin tends to soften as the berries continue to ripen.

Pruning and training: Precise pruning and training requirements for 'Marquis' have not been defined. It is recommended that growers take into account the large cluster size and weight when pruning in order to avoid excessive crop yields. Vines under test in New York and Michigan have been trained to a head about 4 to 5 feet high, and 30 to 40 buds on one-year-old canes are usually retained per vine.

Productivity: Averages 9.0 to 20 tonnes/hectare (very productive) over 5 years in southwestern Michigan.

Fruit analysis: Moderate sugar content with low acidity. Brix and Acidity: Usually 14–19° Brix and acidity below 5 grams/liter.

Flavor: Ripe fruit has very mild labrusca character, but develop a richer fruity American flavor if left to ripen an additional five to ten days.

Usefulness

It is expected that 'Marquis' will be marketed as a seedless table grape based on the cluster size and excellent flavor. Favorable reports on 'Marquis' have been received from northeastern and midwestern grape growing regions. 'Marquis' has not been tested in California. It does not have characteristics suitable for raisin production.

We claim:

1. A new and distinct variety of grapevine herein described and illustrated and identified by the characteristics enumerated above.

* * * * *